(12) United States Patent
Ellis

(10) Patent No.: US 9,456,937 B2
(45) Date of Patent: Oct. 4, 2016

(54) HAND-HELD FEMALE URINE COLLECTOR

(76) Inventor: Ann Marie Ellis, Plymouth, MA (US)

( * ) Notice: Subject to any disclaimer, the term of this patent is extended or adjusted under 35 U.S.C. 154(b) by 298 days.

(21) Appl. No.: 13/308,847

(22) Filed: Dec. 1, 2011

(65) Prior Publication Data

US 2013/0144240 A1 Jun. 6, 2013

(51) Int. Cl.
*A61F 5/455* (2006.01)
*A61F 5/44* (2006.01)
*A61F 13/84* (2006.01)
*A61F 13/472* (2006.01)

(52) U.S. Cl.
CPC ............. *A61F 13/84* (2013.01); *A61F 13/472* (2013.01); *Y10T 29/49826* (2015.01)

(58) Field of Classification Search
CPC ................ A61F 13/472; A61F 13/84; A61F 13/47236; A61F 5/455; A61F 5/4556; A61F 13/551; A61F 2013/8402
USPC ............................................ 604/385.19, 329
See application file for complete search history.

(56) References Cited

U.S. PATENT DOCUMENTS

| | | | |
|---|---|---|---|
| 3,927,426 A | 12/1975 | Geddes | |
| 4,194,508 A | 3/1980 | Anderson | |
| 4,756,029 A * | 7/1988 | Zieve et al. | 4/144.4 |
| 4,904,248 A | 2/1990 | Vaillancourt | |
| 5,091,998 A | 3/1992 | Witzke | |
| 5,243,712 A | 9/1993 | Cross | |
| 5,370,637 A | 12/1994 | Brodeur | |
| D356,865 S | 3/1995 | Ivie | |
| 6,299,606 B1 * | 10/2001 | Young | 604/329 |
| D471,977 S | 3/2003 | Levinson | |
| 6,551,292 B1 * | 4/2003 | D'Acchioli et al. | 604/329 |
| 6,677,498 B2 | 1/2004 | Chen et al. | |
| 6,689,935 B2 | 2/2004 | Chen et al. | |
| 7,569,038 B1 * | 8/2009 | Salem, Jr. | 604/385.13 |
| 7,867,623 B2 | 1/2011 | Ziemer et al. | |
| 7,896,857 B2 | 3/2011 | Kay et al. | |
| 8,292,863 B2 * | 10/2012 | Donoho | 604/385.06 |
| 8,403,903 B2 * | 3/2013 | Clark et al. | 604/385.02 |
| 2004/0122402 A1 * | 6/2004 | McDaniel | 604/385.17 |
| 2004/0249079 A1 * | 12/2004 | Funk et al. | 525/191 |

(Continued)

FOREIGN PATENT DOCUMENTS

| | | |
|---|---|---|
| EP | 0464575 A1 | 1/1992 |
| EP | 0558351 A1 | 2/1993 |

(Continued)

OTHER PUBLICATIONS

Google Search #1 Downloaded May 26, 2011—http://www.pooshka.com/a.php?aid=2726&watch=1 "Female Urination Device for Outdoors Women".

(Continued)

*Primary Examiner* — Susan Su

(57) ABSTRACT

A portable female urine collector for urine collection and stowage, and a method of assembling same is disclosed. In one embodiment, the portable female urine collector includes a fordable absorbent pad for collecting urine, and a receptacle attached to the foldable absorbent pad for stowing the foldable absorbent pad therein after the foldable absorbent pad is used to collect urine. After the foldable absorbent pad is used, the foldable absorbent pad is folded by the user and then sealed within the attached receptacle for later disposal. The portable female urine collector is useful whenever toilet facilities for females are either unavailable or unsuitable.

14 Claims, 22 Drawing Sheets

(56) References Cited

U.S. PATENT DOCUMENTS

| | | | |
|---|---|---|---|
| 2004/0254547 A1* | 12/2004 | Okabe et al. | 604/317 |
| 2005/0256487 A1* | 11/2005 | Williams | 604/385.19 |
| 2007/0192948 A1* | 8/2007 | Ernest et al. | 4/144.2 |
| 2008/0071239 A1* | 3/2008 | Nandrea et al. | 604/361 |
| 2008/0132861 A1* | 6/2008 | Tomes et al. | 604/367 |
| 2009/0048569 A1 | 2/2009 | Salehi | |
| 2012/0103347 A1* | 5/2012 | Wheaton et al. | 128/885 |

FOREIGN PATENT DOCUMENTS

| | | |
|---|---|---|
| EP | 0887061 A1 | 6/1997 |
| EP | 0806194 A1 | 11/1997 |
| WO | 9507671 | 3/1995 |
| WO | 9843563 | 10/1998 |
| WO | 0000132 | 1/2000 |
| WO | 2007050716 | 5/2007 |
| WO | 2009023878 A1 | 2/2009 |

OTHER PUBLICATIONS

Google Search #2 Downloaded May 25, 2011—http://www.bag-bath.com/uk/pibella_-_travel.htm.

Google Search #3 Downloaded May 26, 2011—http://thepstyle.com/pages/pstyle.

\* cited by examiner

HAND-HELD FEMALE URINE COLLECTOR

FIELD OF THE INVENTION

This invention generally relates to urine collectors, and more particularly relates to female urine collectors and methods of assembling same.

BACKGROUND OF THE INVENTION

It sometimes may be necessary for a female to urinate without availability of suitable toilet facilities. Such a situation may arise, for example, if the female is hiking or camping in a wilderness area, skiing, snowmobiling, caving, taking biking trips, at the beach when a bath house is miles away, at outdoor functions, at sporting events and other situations. As another example, such a situation may arise when a female athlete is participating in sports on a sports field where there may not be a near-by portable toilet facility or locker room toilet facility. In addition, such a situation may arise if the female finds herself in a transportation conveyance (e.g., small airplane, automobile traveling a long distance through an isolated area, U.S. Postal Service® vehicle delivering mail, UPS® or Federal Express® vehicle delivering packages or other conveyance) lacking suitable public toilet facilities. The registered mark "U.S. Postal Service)" is owned by the United States Postal Service located in Washington, D.C., U.S.A. The registered mark "UPS®" is owned by United Parcel Service, Incorporated located in Sandy Springs, Georgia, U.S.A. The registered mark "Federal Express®" is owned by FedEx Corporation, located in Memphis, Tenn., U.S.A. As yet another example, such a situation may arise when an act of nature or natural disaster strikes, such as an earthquake or hurricane, making water or toilet facility use unavailable. However, even when public toilet facilities are available, the available public toilet facilities may not be suitable because, due to public use of the public toilet facilities, the available public toilet facilities might be unclean, contaminated with bacteria or otherwise unsanitary.

Moreover, even when a suitable toilet facility is nearby, it may not be possible for the female to use the toilet facility. This situation may occur if the female is bedridden or otherwise not ambulatory and use of a bed pan is undesirable or not possible. Further, such a situation may arise when a female is involved in a military combat operation or other military setting where immediate use of any nearby toilet facility is not advisable or possible because of a risk to personal safety. In addition, in some underdeveloped or "third-world" countries, availability of toilet facilities suitable for females is severely limited.

When using a toilet facility, a female will typically sit on a toilet seat. However, sitting on a contaminated toilet seat, such as a contaminated toilet seat in a public toilet facility, can lead to transmission of disease. Diseases that have been associated with contaminated toilet seats include herpes, trichomonas vaginalis (i.e., a protozoan parasite that causes vaginitis), gonorrhea, gastroenteritis (i.e., severe inflammation of the gastrointestinal tract caused by contact with contaminated water) and other diseases. Females may be at a higher risk of contracting these diseases because females will typically sit on a toilet seat when using the toilet facility.

As previously mentioned, a female may find herself in a wilderness environment, such as when skiing, snowmobiling or the like. In cold temperatures, an individual (male or female) will typically be covered in layers of clothing. A male can conveniently relieve himself in a standing position by means of a zippered opening in the crotch area of his clothing. However, a female is usually required to remove a substantial amount of at least a lower portion of her clothing and then assume a squatting position to relieve herself. This procedure exposes a substantial portion of the female anatomy to outdoor elements as well as compromises her privacy. It is desirable for the female to avoid exposing a substantial portion of her anatomy to outdoor elements and also desirable for her to preserve her privacy.

Female urine management devices are known. For example, a funnel device to facilitate urination by women in an upright position includes a semi-rigid funnel rim contoured to surround the female genital region. A flexible funnel body depends from the rim and is sealed to the rim around the circumference. The funnel body has a continuous wall sloped inwardly and towards the front of the funnel body. The funnel body terminates in an orifice situated toward the front of the funnel body. A bendable, elongated disposal tube is sealably attached to the funnel orifice and is inclined downward and outward at an angle with regard to the funnel body. The tube is circumferentially corrugated to enable bending for storage and for directing urine flow. However, this device does not appear to provide for collection and subsequent disposal of the urine. Thus, this device may not be useable, for example, in the previously mentioned transportation conveyances where toilet facilities are unavailable.

Another known device is a disposable absorbent article which is substantially flat prior to use for wearing adjacent a body discharge area. The disposable absorbent article comprises a liquid pervious top sheet, a back sheet joined to said top sheet and an absorbent core intermediate the back sheet and the top sheet. The absorbent core comprises means for expanding the article into a tridimensional structure while being worn by a user. The means is activated by body fluids. The absorbent article further comprises an odor-control material comprising one or more odor-control agents. However, this device is not easy to handle and place near the body discharge area. Also, this device is not conveniently disposed of after urine has been collected, creating an awkward situation in the absence of an easily accessible trash receptacle.

SUMMARY OF THE INVENTION

The present invention addresses the shortcomings of the prior art approaches mentioned hereinabove by providing a portable female urine collector for urine collection and stowage and a method of assembling same, as described and claimed herein.

More specifically, the portable female urine collector of the present invention includes an attached receptacle that enables a urine-absorbent pad belonging to the portable female urine collector to be fully received into the receptacle and enclosed therein without leaking urine. Fully receiving and enclosing the urine-absorbent pad in the receptacle after use thereof allows the urine-absorbent pad to be stowed until eventual proper disposal, so as not to litter the environment.

Also, the female urine collector of the present invention is composed of a relatively soft material that is foldable, collapsible, and sized or configured to be portable. The portability of the female urine collector allows a user thereof to conveniently carry the portable female urine collector on her person. This is particularly desirable when the user is hiking, camping, skiing, snowmobiling, caving, taking biking trips, at the beach when a bath house is not nearby, at outdoor functions, attending sporting events, participating in sports on an athletic field, and in other situations. The portable female urine collector is also useful when the female finds herself in a transportation conveyance (e.g., small airplane, automobile traveling a long distance through an isolated area, U.S. Postal Service® vehicle delivering mail, UPS® or Federal Express® vehicle delivering packages, or other conveyance) lacking suitable toilet facilities, or when use of public toilet facilities is undesirable or not possible. In addition, use of the portable female urine collector is useful in hospital settings when use of a bed pan is not desirable or possible. Also, use of the portable female urine collector is useful when a female is involved in a military combat operation, or other military setting where immediate use of any nearby toilet facility is not advisable or possible because of a risk to personal safety. Use of the portable female urine collector of the present invention may also be advisable in other situations, such as in underdeveloped or "third world" countries, where availability of toilet facilities suitable for females is severely limited.

A general aspect of the invention is a portable female urine collector for urine collection and stowage, the portable female urine collector including: a foldable absorbent pad for collecting urine; and a receptacle, coupled to the foldable absorbent pad, the receptacle being for stowing the foldable absorbent pad therein after the foldable absorbent pad has been used to collect urine from a female.

In some embodiments, the foldable absorbent pad is adapted to assume an unfolded state before collecting the urine; and the foldable absorbent pad is adapted to assume a folded state after collecting the urine.

In some embodiments, the foldable absorbent pad includes a plurality of layers. In other embodiments, the plurality of layers include: a urine-permeable first layer for wicking the urine away from a urine discharge area of the user; a urine-absorbing second layer intimately contacting the urine-permeable first layer for absorbing the urine wicked away from the urine discharge area of the user; and a urine-impermeable third layer disposed adjacent to the urine-absorbing second layer for restricting the urine to the urine-absorbing second layer. In further embodiments, the urine-absorbing second layer includes an absorbent powder. In other further embodiments, the urine-absorbing second layer includes an absorbent gel. In yet other further embodiments, the urine-absorbing second layer is spirally-wound for spirally expanding as the urine-absorbing second layer absorbs the urine; and the urine-impermeable third layer is contoured to expand as the urine-absorbing second layer spirally expands. In still other further embodiments, the urine-absorbing second layer is disk-shaped for radially axially expanding as the urine-absorbing second layer absorbs the urine; and the urine-impermeable third layer is contoured to expand as the urine-absorbing second layer radially axially expands. In other further embodiments, the urine-absorbing second layer includes a plurality of disks stacked one upon the other for sequentially absorbing the urine and for sequentially expanding as the plurality of disks sequentially absorb the urine; and the urine-impermeable third layer is contoured to expand as the plurality of disks sequentially expand.

In some embodiments, the receptacle is adapted to assume an unexpanded state during urine collection for unobstructed collection of the urine; and wherein the receptacle is adapted to assume an expanded state after urine collection for stowing the foldable absorbent pad in the receptacle.

In some embodiments the receptacle is configured as a pocket guide for facilitating placement of the foldable absorbent pad at a urine discharge area of the user.

In some embodiments, the foldable absorbent pad defines a wiping surface thereon for wiping the urine away from a urine discharge area of the user.

Another general aspect of the invention is a portable female urine collector for urine collection and stowage, the portable female urine collector including: a foldable absorbent pad for collecting urine by absorbing the urine, the foldable absorbent pad including: a urine-permeable first layer for wicking the urine away from a urine discharge area of a user; an expandable urine-absorbing second layer intimately contacting the urine-permeable first layer for absorbing the urine wicked away from the urine discharge area of the user, the urine-absorbing second layer being adapted to expand as the urine-absorbing second layer absorbs the urine; a urine-impermeable third layer disposed immediately adjacent to the urine-absorbing second layer for restricting the urine to the urine-absorbing second layer, the urine-impermeable third layer being adapted to expand as the urine-absorbing second layer absorbs the urine and expands; and a receptacle connected to the foldable absorbent pad for stowing the foldable absorbent pad therein after the foldable absorbent pad has collected urine and has been folded.

In some embodiments, the foldable absorbent pad can assume an unfolded state before collecting the urine; and the foldable absorbent pad can assume a folded state after collecting the urine. In further embodiments, the urine-absorbing second layer includes an absorbent powder. In other further embodiments, the urine-absorbing second layer includes an absorbent gel. In other further embodiments, the urine-absorbing second layer is spirally wound for spirally expanding as the urine-absorbing second layer absorbs the urine; and the urine-impermeable third layer is contoured to expand as the urine-absorbing second layer spirally expands. In other further embodiments, the urine-absorbing second layer is disk-shaped for radially and axially expanding as the urine-absorbing second layer absorbs the urine; and the urine-impermeable third layer is contoured to expand as the urine-absorbing second layer radially and axially expands. In other further embodiments, the urine-absorbing second layer includes a plurality of disks stacked one upon the other for sequentially absorbing the urine and for sequentially expanding as the plurality of disks sequentially absorb the urine; and the urine-impermeable third layer is contoured to expand as the plurality of disks sequentially expand.

Another general aspect of the invention is a method of assembling a portable female urine collector for urine collection and stowage, the method including: providing a foldable absorbent pad for collecting urine; and coupling a receptacle to the foldable absorbent pad capable of stowing the foldable absorbent pad therein after the foldable absorbent pad has collected urine.

BRIEF DESCRIPTION OF THE DRAWINGS

The invention will be more fully understood by reference to the detailed description in conjunction with the following figures, wherein size of various parts may be exaggerated for clarity, and wherein.

DETAILED DESCRIPTION OF PREFERRED EMBODIMENTS

Figure 1:
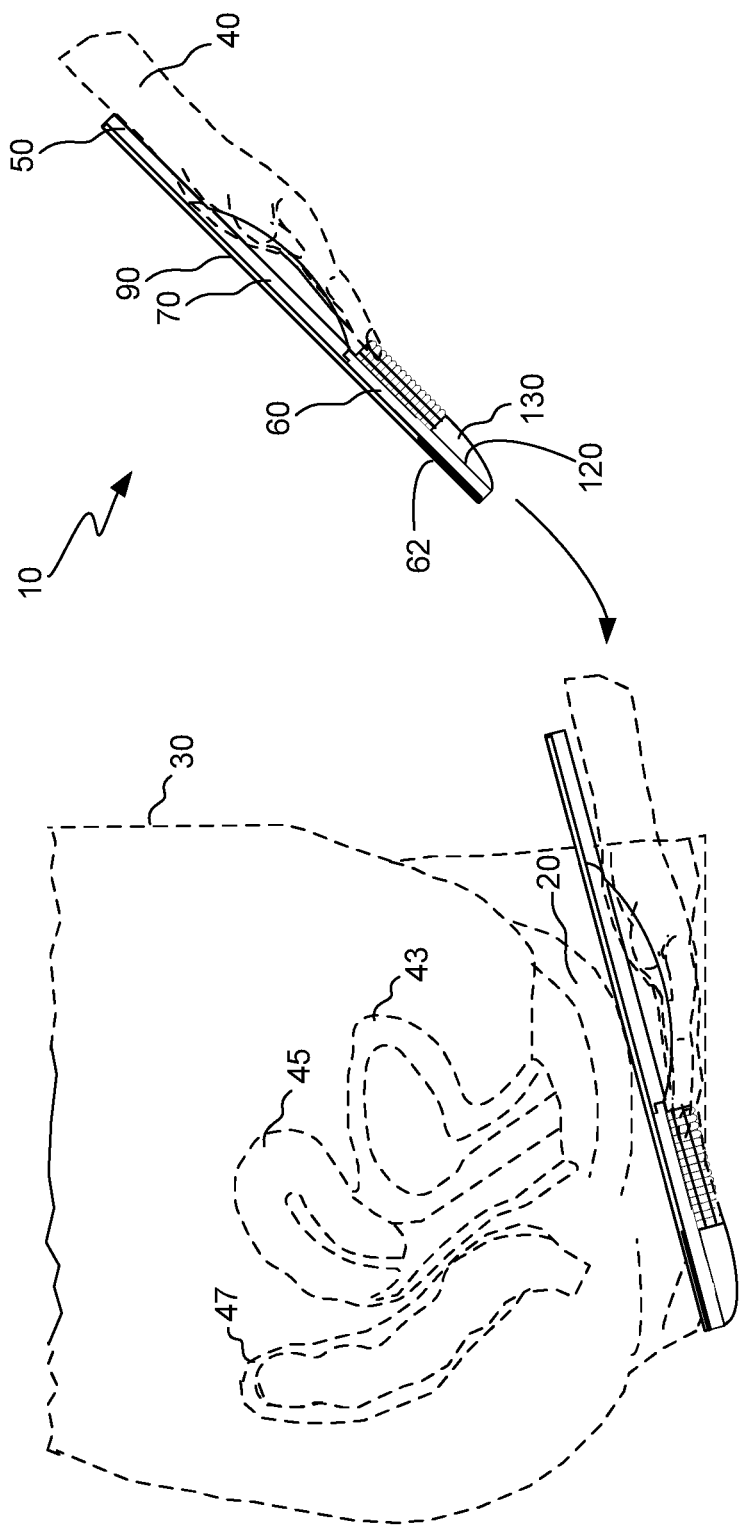
FIG. 1 is a view in elevation of a first embodiment portable female urine collector being placed by a user on a urine discharge area of the user.
Figure 2:
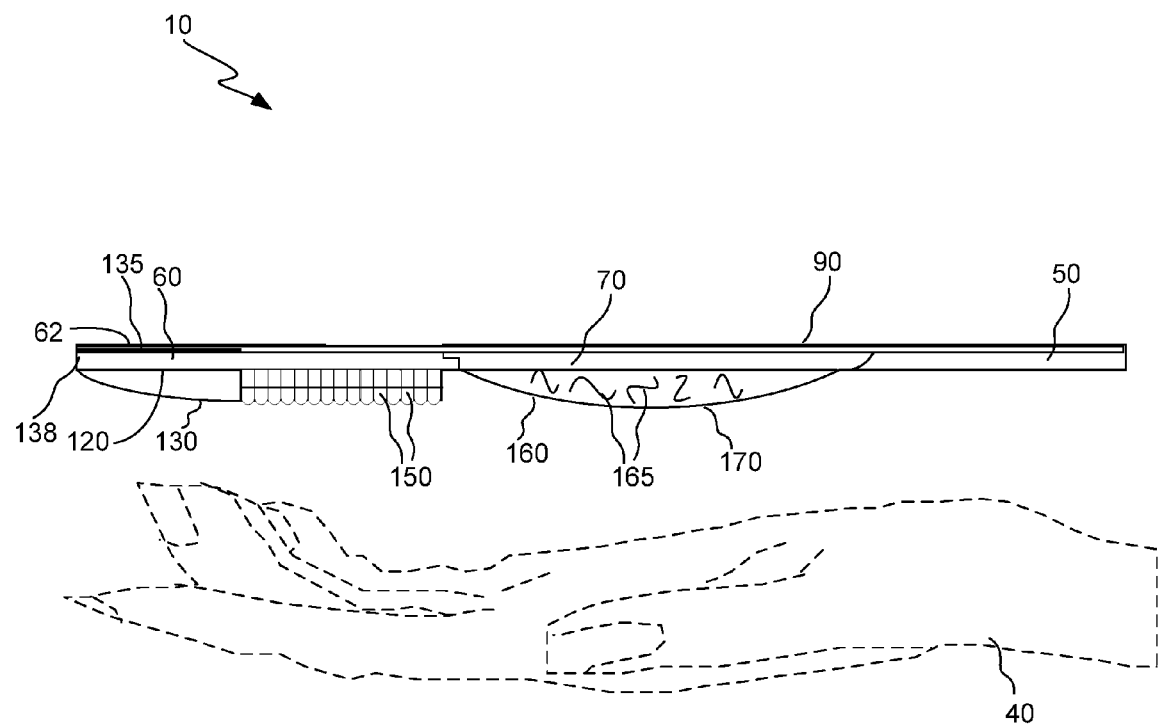
FIG. 2 is a view in elevation of the first embodiment portable female urine collector, this view showing the compact size of the first embodiment portable female urine collector compared to the size of a human hand.
Figure 3:
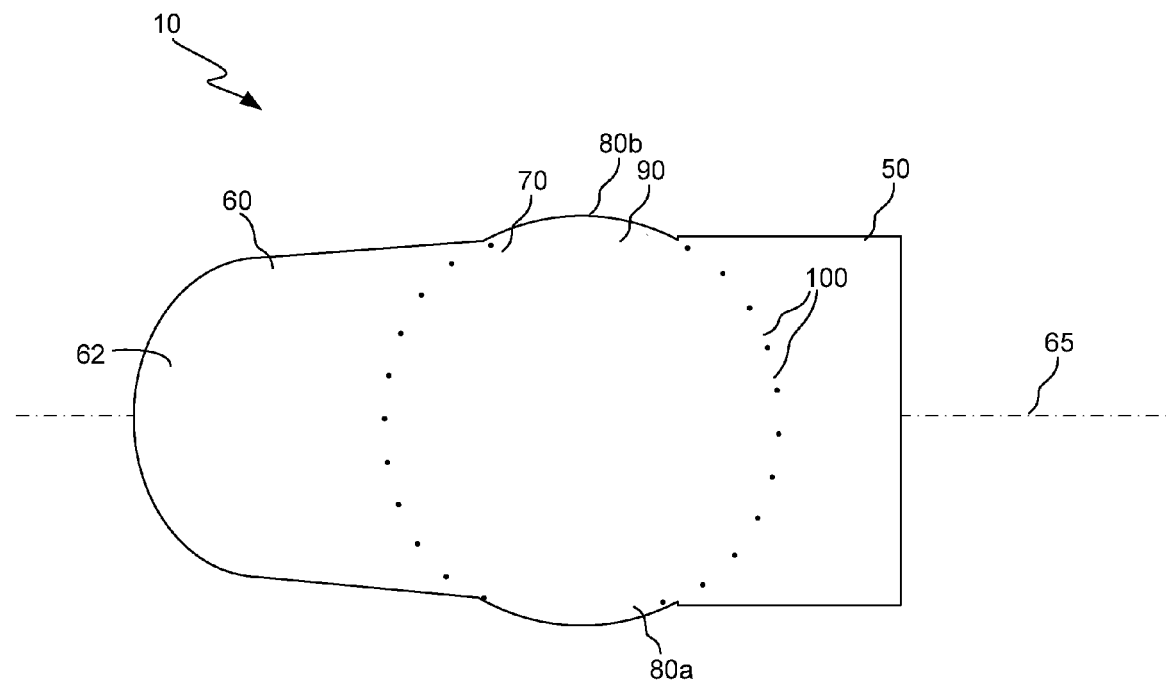
FIG. 3 is a top plan view of the first embodiment portable female urine collector.
Figure 4:
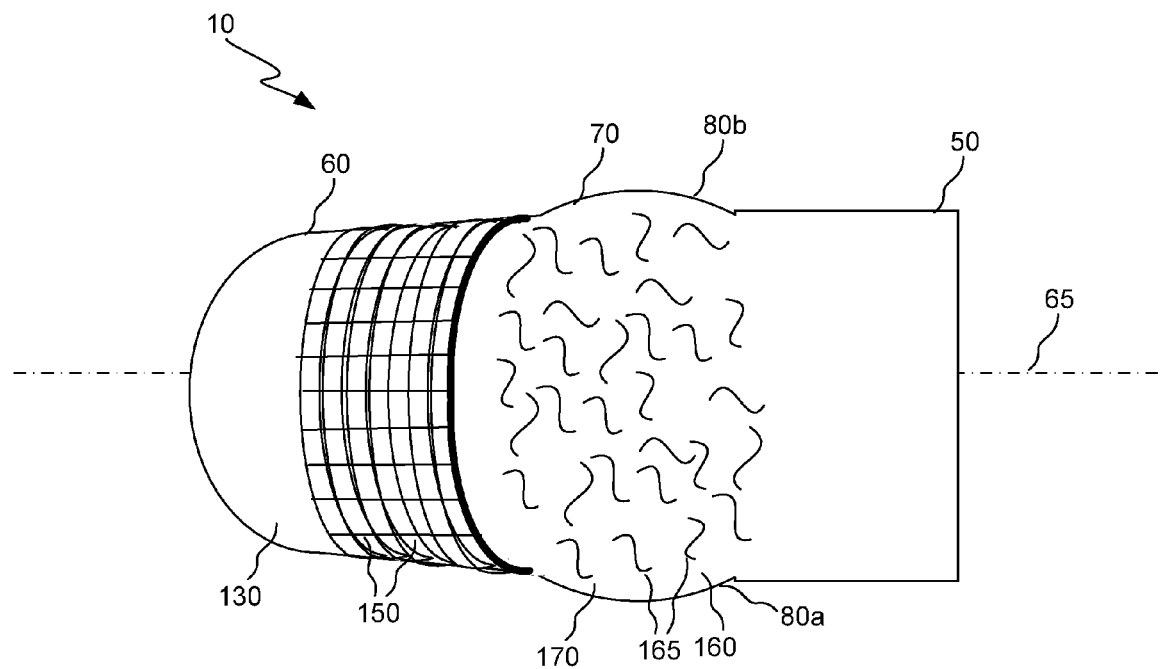
FIG. 4 is a bottom plan view of the first embodiment portable female urine collector, this view showing a receptacle belonging to the first embodiment portable female urine collector.
Figure 5:
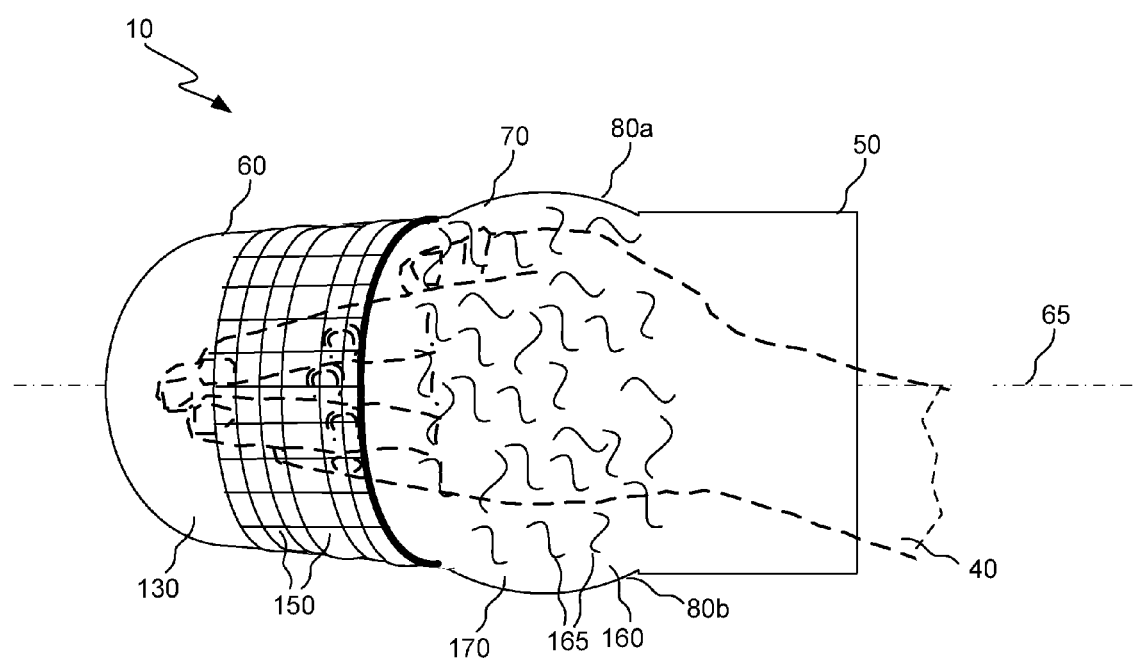
FIG. 5 is another bottom plan view of the first embodiment portable female urine collector, this view showing the hand of the user inserted into the receptacle.
Figure 6:
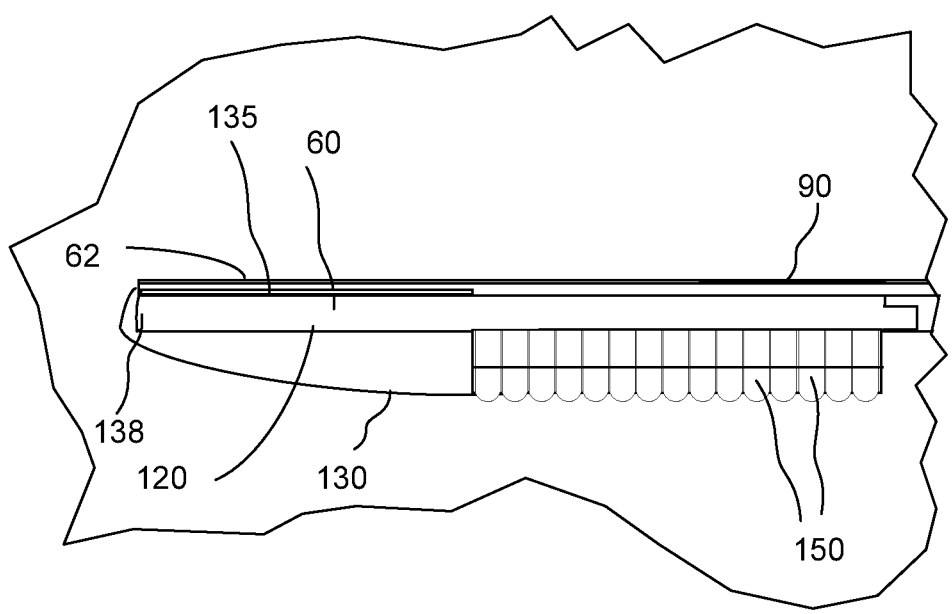
FIG. 6 is a fragmentary view in elevation of a distal end portion of the first embodiment portable female urine collector, this view showing a receptacle attached to an absorbent pad belonging to the first embodiment portable female urine collector.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from either the spirit or scope of the invention.

In addition, the present patent specification uses formal outline headings for clarity of presentation. However, it is to be understood that the outline headings are for presentation purposes, and that different types of subject matter may be discussed throughout the application (e.g., device(s)/structure(s) may be described under process(es)/operations heading(s) and/or process(es)/operations may be discussed under structure(s)/process(es) headings; and/or descriptions of single topics may span two or more topic headings). Hence, the use of the formal outline headings is not intended to be in any way limiting.

Therefore, with reference to FIG. 1, there is shown a first embodiment portable female urine collector, generally referred to as 10, for urine collection and stowage. As described in detail hereinbelow, first embodiment portable female urine collector 10 (hereinafter referred to as "first embodiment urine collector 10") is adapted to be placed at a urine discharge area 20 of a female user 30 (hereinafter referred to as "user 30"). As described in detail hereinbelow, first embodiment urine collector 10 is adapted to be easily manipulated by means of a hand 40 of user 30 for placement of first embodiment urine collector 10 at urine discharge area 20. The urine discharge area 20 receives urine from a bladder 43 located near a female reproductive organ 45 and an intestine 47 of user 30, as shown. Also, as described in detail hereinbelow, first embodiment urine collector 10 is adapted to absorb the urine and stow the urine therein for subsequent disposal.

Referring to FIGS. 1, 2, 3, and 4, first embodiment urine collector 10 includes a proximal end portion 50 and a distal end portion 60 disposed opposite proximal end portion 50. Proximal end portion 50 may be generally rectangularly-shaped for providing a support platform for the heel of hand 40 and distal end portion 60 may be generally tapered and oblong in shape with a rounded end for facilitating placement of first embodiment urine collector 10 into the generally confined space surrounding urine discharge area 20. Distal end portion 60 includes a portion thereof having a top wiping surface 62 for wiping residual urine from urine discharge area 20 after urine discharge therefrom. Proximal end portion 50 and distal end portion 60 are coaxially aligned along a common longitudinal axis 65. In addition, proximal end portion 50 and distal end portion 60 are also necessarily flexible for comfortably conforming to the body contour of urine discharge area 20. Moreover, proximal end portion 50 and a center portion 70 are foldable toward distal end portion 60 for ease of disposal, as described in detail hereinbelow. Center portion 70 is interposed between proximal end portion 50 and distal end portion 60. In order to facilitate the desired flexibility, proximal end portion 50 and distal end portion 60 may be made of any suitable flexible and foldable material, such as, without limitation, a suitable fabric or fiber material. Such a suitable fabric or fiber material may be cotton, polyester, a polymer plastic, paper or the like. Previously mentioned center portion 70 is adapted to absorb urine, as described in detail hereinbelow. Center portion 70 may include at least two laterally outwardly extending wings or flaps 80a and 80b, if desired. Flaps 80a and 80b can serve as urine splash guards.

Referring again to FIGS. 1, 2, 3, and 4, covering a top surface of center portion 70 and connected thereto is a urine pervious or permeable first layer 90 for "wicking" urine away from urine discharge area 20. Wicking urine away from urine discharge area 20 facilitates keeping urine discharge area 20 dry and comfortable for user 30. First layer 90 may be connected to the top surface of center portion 70 such as by means of a suitable, nonirritating adhesive (not shown) or by means of a plurality of threads or stitches 100. Alternatively, first layer 90 may also cover proximal end portion 50 and distal end portion 60, if desired. The terminology "wicking" is defined herein to mean the act of moving moisture by capillary action from a surface of a material to an interior of the material. The wicking material comprising first layer 90 is a porous, hydrophilic material. In this regard, the wicking material comprising first layer 90 may be, without limitation, cotton, wool, a mixture of glass fiber and cellulose, polyester, any polypropylene non-woven fabric, "TEFLON®" or other suitable material. TEFLON®, which comprises polytetrafluoroethylene, is a registered mark owned by E.I. du Pont de Nemours and Company located in Wilmington, Del., U.S.A. As urine is wicked away from urine discharge area 20 and through first layer 90, the urine will be absorbed into an expandable second layer 110 (e.g., see FIG. 7) in a manner disclosed in detail hereinbelow.

Referring to FIGS. 1, 2, 4, 5, 6. and 7, connected to a bottom surface 120 of distal end portion 60 is an expandable encasement, pocket, bag or receptacle 130 for manipulating first embodiment urine collector 10 onto urine discharge area 20 and for stowing center portion 70, distal end portion 60 and proximal end portion 50 in receptacle 130 following urine collection. By way of example only and not by way of limitation, receptacle 130 may be approximately 25.4 centimeters (i.e., 10 inches) to approximately 30.5 centimeters (i.e., 12 inches) in length. Approximately 7.6 centimeters (i.e., three inches) of the length of receptacle 130, as measured from the tapered end of distal end portion 60, is affixed to and embedded in distal end portion 60, so as to be affixed to distal end portion 60 for reasons to become apparent hereinbelow. More specifically, receptacle 130 has an end portion 135 embedded between first layer 90 and distal end portion 60. End portion 135 is affixed between first layer 90 and distal end portion 60 by any suitable connecting means, such as by a suitable, non-toxic permanent adhesive (not shown). Such a non-toxic permanent adhesive suitable for use with the invention should be free from formaldehyde, hydrocarbons, synthetic chemicals, petrochemical and be water-based. A remaining portion of receptacle 130 that is not embedded between first layer 90 and distal end portion 60 downwardly distends and wraps around an end 138 of distal end portion 60, such that the remaining portion of receptacle 130 is received against bottom surface 120 of distal end portion 60. More specifically, this remaining portion of receptacle 130 spans bottom surface 120 of distal end portion 60 and is affixed thereto by means of a suitable, non-toxic adhesive (not shown) or other suitable connecting means. If an adhesive is used, the adhesive is selected such that this remaining portion of receptacle 130 is capable of being manually detached from bottom surface 120 for reasons disclosed hereinbelow. Receptacle 130 may be a fabric made of any suitable material, such as, without limitation, cotton, wool, polyester, and elastomer or other material.

Referring again to FIGS. 1, 2, 4, 5, 6. and 7, and as described more fully hereinbelow, receptacle 130 defines a pocket or chamber 140 therein for receiving hand 40. In this manner, hand 40 uses receptacle 130 to precisely guide or maneuver first embodiment urine collector 10 to urine discharge area 20 and, therefore, serves as a pocket guide. In addition, receptacle 130 has a plurality of flexible longitudinally and transversely extending folds, creases or ribs 150 for facilitating expansion of receptacle 130 when hand 40 is inserted into chamber 140. As described more fully hereinbelow, ribs 150 also facilitate expansion of receptacle 130 when proximal end portion 50, distal end portion 60 and center portion 70 are folded and stowed in receptacle 130 following urine collection. Thus, receptacle 130 and associated ribs 150 advantageously serve a dual purpose. That is, receptacle 130 and associated ribs 150 serve the dual purpose of providing means for precisely guiding or maneuvering first embodiment urine collector 10 to urine discharge area 20 and also means for storing center portion 70, distal end portion 60 and proximal end portion 50 following urine collection. First embodiment urine collector 10 also includes a "crinkled surface" 160 thereon, as described in detail hereinbelow. The terminology "crinkled surface" means a surface having a topography that includes a multiplicity of irregularly-shaped ripples or wrinkles 165.

Figure 7:
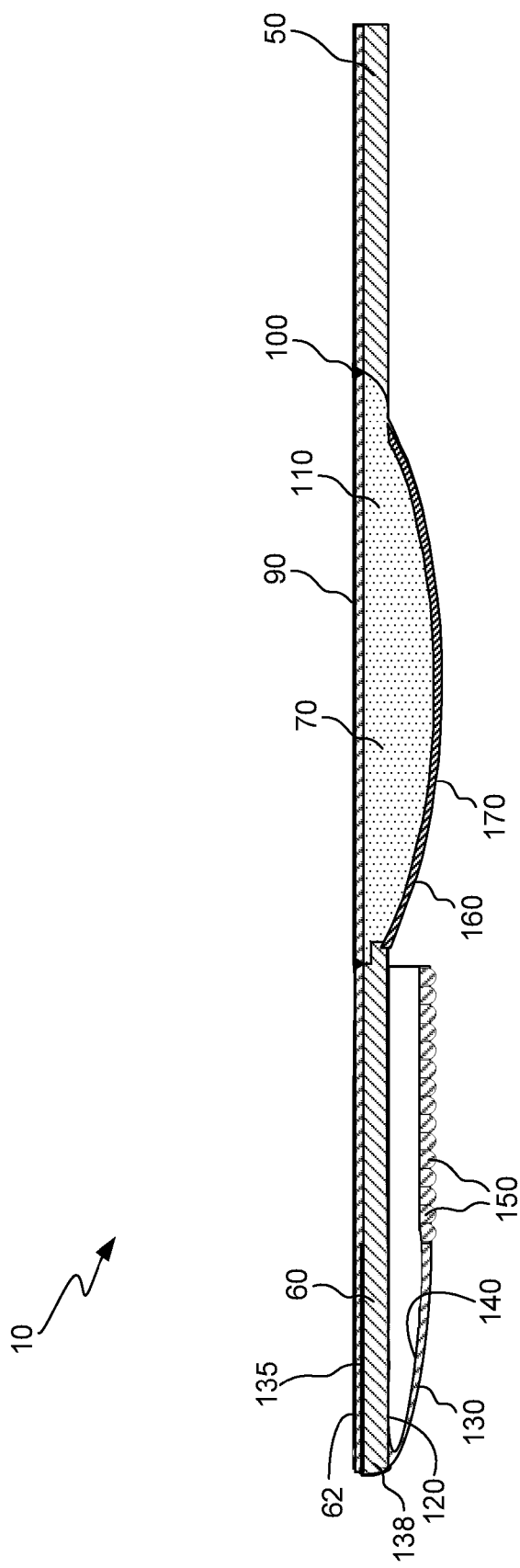
FIG. 7 is a view in vertical section of the first embodiment portable female urine collector, this view showing a one-piece, urine absorbent middle layer interposed between a urine pervious top layer and a urine impervious bottom layer.

Referring to FIG. 7, previously mentioned urine-absorbing second layer 110 is in intimate fluid contact with urine-permeable first layer 90 and is interposed between first layer 90 and a urine-impervious or urine-impermeable third layer 170. The third layer 170 is expandable and sealably surrounds second layer 110 in a manner and for reasons provided presently. In addition, third layer 170 may include an odor-control agent for masking the odor of the urine. The odor-control agent may be a known aromatic odor control agent, such as, without limitation, a phenolic compound.

Second layer 110 may be made of any suitable hydrophilic, urine-absorbing powder, such as fluffed cellulose pulp fibers or other suitable fiber-based material. When fiber-based material is used, the urine retention capacity may be about 20 times the weight of the fiber-based material. By way of example only, and not by way of limitation, the amount of powder present may be from about three to about five grams (i.e., from about 0.10 to about 0.17 ounces). Alternatively, second layer 110 may be made from any suitable and well-known super absorbing polymer, such as, without limitation, sodium polyacrylate, polyacrylamide copolymer, ethylene maleic anhydride copolymer, potassium acrylate, an alkyl acrylate, cross-linked carboxymethylcellulose or other super absorbing polymer. When a super absorbing polymer is used, the urine retention capacity may be about 400 times the weight of the super absorbing polymer. Use of the fiber-based material may be preferable to use of polymer-based materials when the slower rate of biodegradability of polymer-based materials in landfills is of concern. Thus, it may be appreciated that the present invention advantageously provides the option of using either fiber-based or polymer-based absorbent material in second layer 110. Moreover, the powder substances mentioned hereinabove may bind with the urine and form a gel-like substance when the urine comes into contact with the powder. Such a gel-like substance will capture and hold the urine in second layer 110. On the other hand, the material comprising second layer 110 initially may be a super absorbent gel material rather than initially a powder. In this instance, the super absorbent gel material may be any one of a number of known hydrogels, which may be natural or synthetic polymers. The previously mentioned third layer 170 is made of a nonporous, hydrophobic material, such as polyethylene film. The previously mentioned wrinkles 165 formed in crinkled surface 160 that belongs to third layer 170, allows the hydrophobic material of third layer 170 to outwardly enlarge or expand as second layer 110 absorbs urine and expands.

Figure 8:
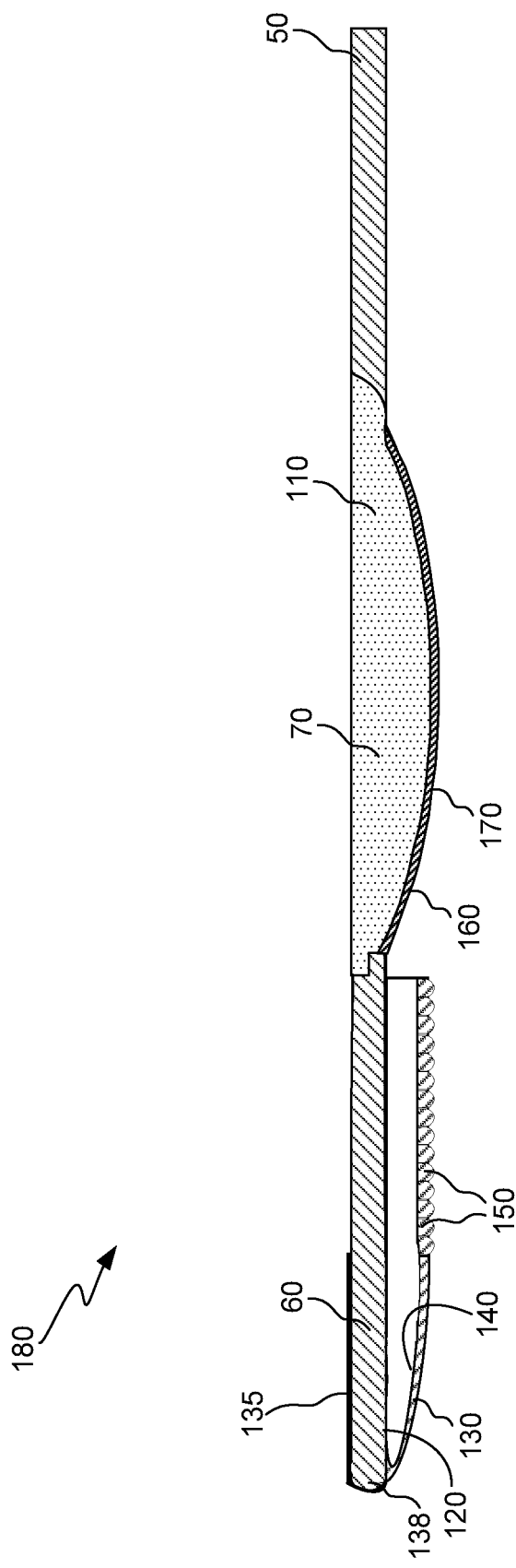
FIG. 8 is a view in vertical section of a second embodiment portable female urine collector, this view illustrating absence of the urine pervious top layer; but, showing presence of the one-piece, urine absorbent layer and the urine impervious bottom layer.

As best seen in FIG. 8, there is shown a second embodiment portable female urine collector, generally referred to as 180, for urine collection and stowage. Second embodiment portable female urine collector 180 (herein referred to as "second embodiment urine collector 180") is substantially similar to first embodiment urine collector 10, except first layer 90 is absent. In this embodiment, second layer 110 will necessarily contact the skin of user 30 in urine discharge area 20. Therefore, it is important that the material comprising second layer 110 be non-toxic, chemically benign and non-irritating to the skin of user 30. To accomplish this result, the material comprising second layer 110 may be cotton, wool or like material. Second embodiment urine collector 180 provides an alternative embodiment to first embodiment urine collector 10.

Figure 9:
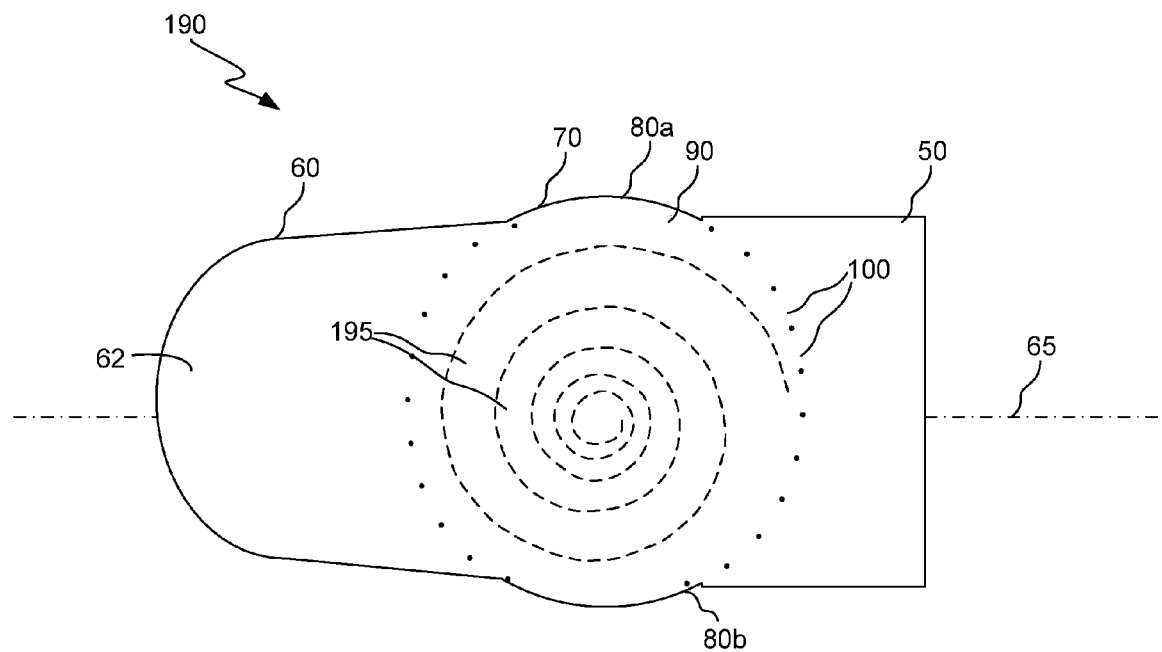
FIG. 9 is a top plan view of a third embodiment portable female urine collector, this view showing in phantom a spirally-wound urine absorbent middle layer.
Figure 10:
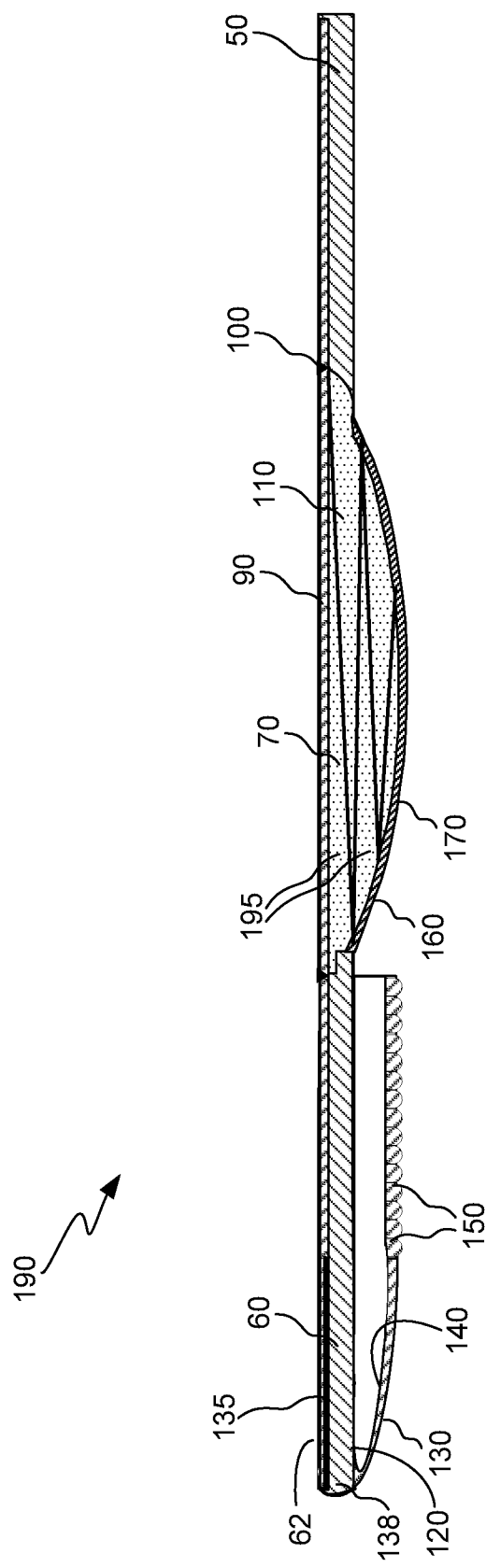
FIG. 10 is a view in vertical section of the third embodiment portable female urine collector, this view showing the spirally-wound urine absorbent middle layer in vertical section.

Referring to FIGS. 9 and 10, there is shown a third embodiment portable female urine collector, generally referred to as 190, for urine collection and stowage. Third embodiment portable female urine collector 190 (herein referred to as "third embodiment urine collector 190") is substantially similar to first embodiment urine collector 10, except second layer 110 is spirally-wound for spirally expanding as urine-absorbing second layer 110 absorbs the urine. In this regard, second layer 110 includes integrally formed spiral portions 195 that possess a swirl-like configuration in the direction of third layer 170 to intimately engage and expand third layer 170 as second layer 110 expands due to urine uptake. Third embodiment urine collector 190 provides an alternative embodiment to first embodiment urine collector 10.

Figure 11:
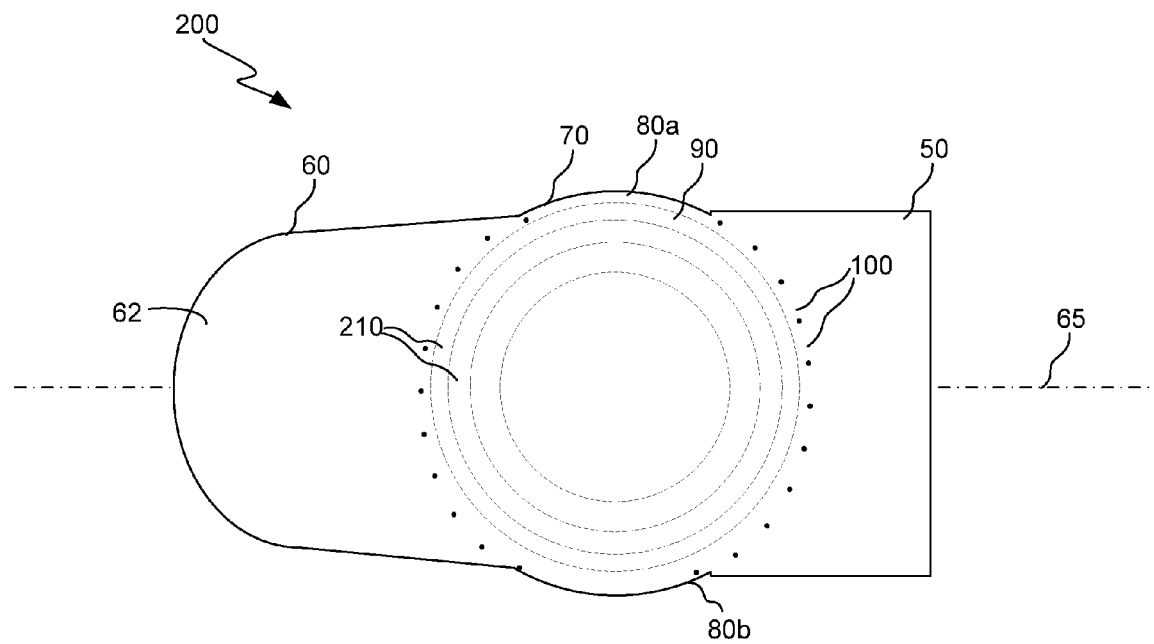
FIG. 11 is a top plan view of a fourth embodiment portable female urine collector, this view showing in phantom a urine-absorbing second layer including a plurality of circular disks of decreasing diameters stacked one upon the other.
Figure 12:
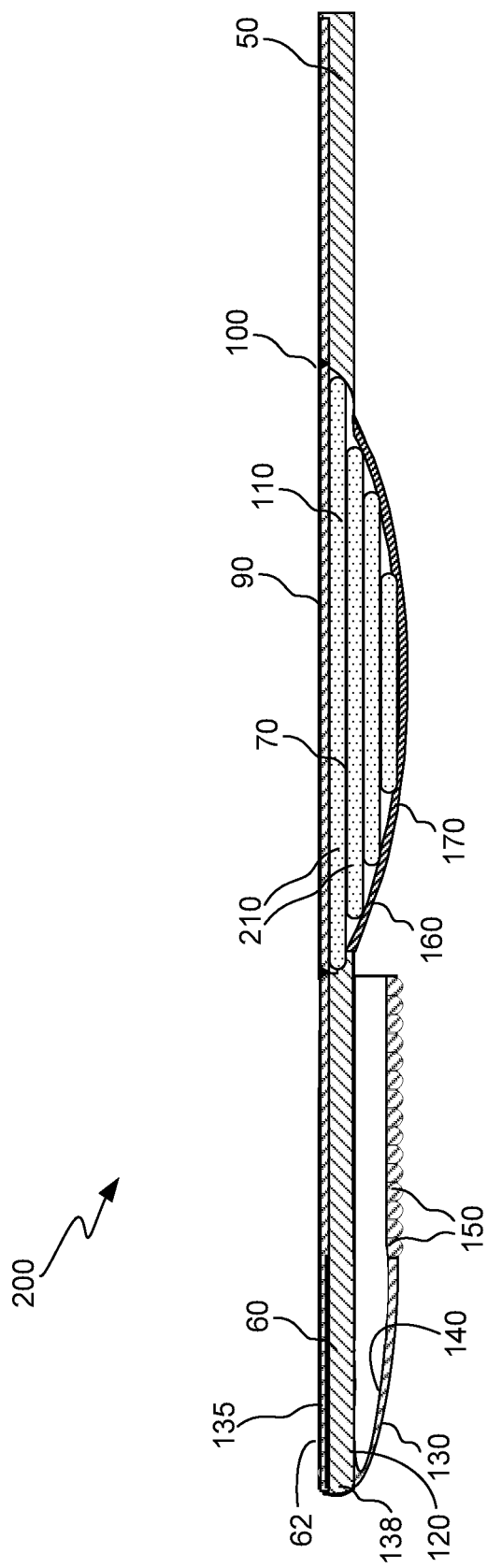
FIG. 12 is a view in vertical section of the fourth embodiment portable female urine collector, this view showing the urine-absorbing second layer including the plurality of circular disks of decreasing diameters stacked one upon the other.
Figure 13:
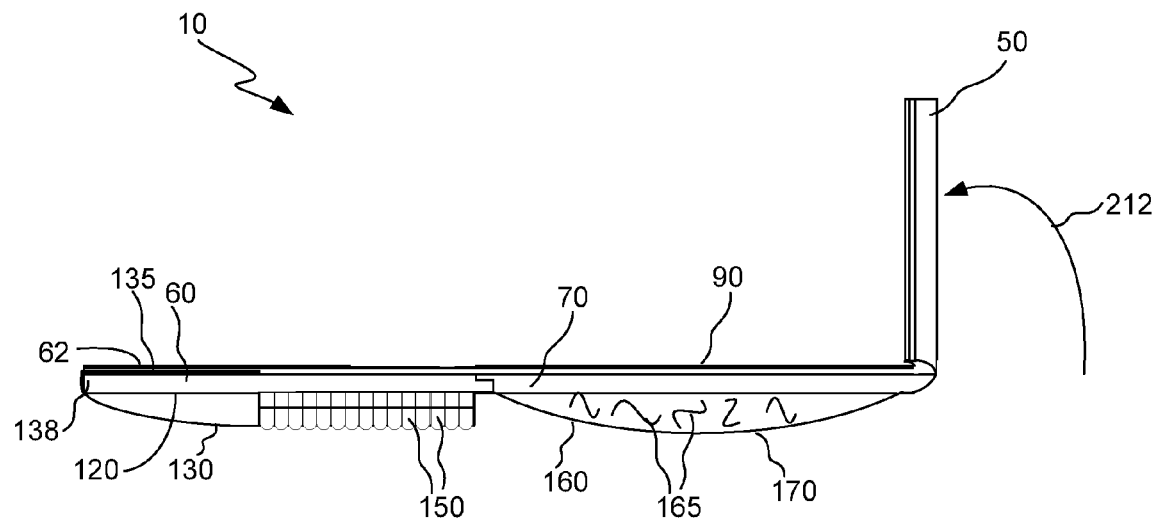
FIG. 13 is a view in elevation of the first embodiment portable female urine collector, this view showing a proximal end portion of the portable female urine collector being folded toward a center portion of the portable female urine collector.
Figure 14:
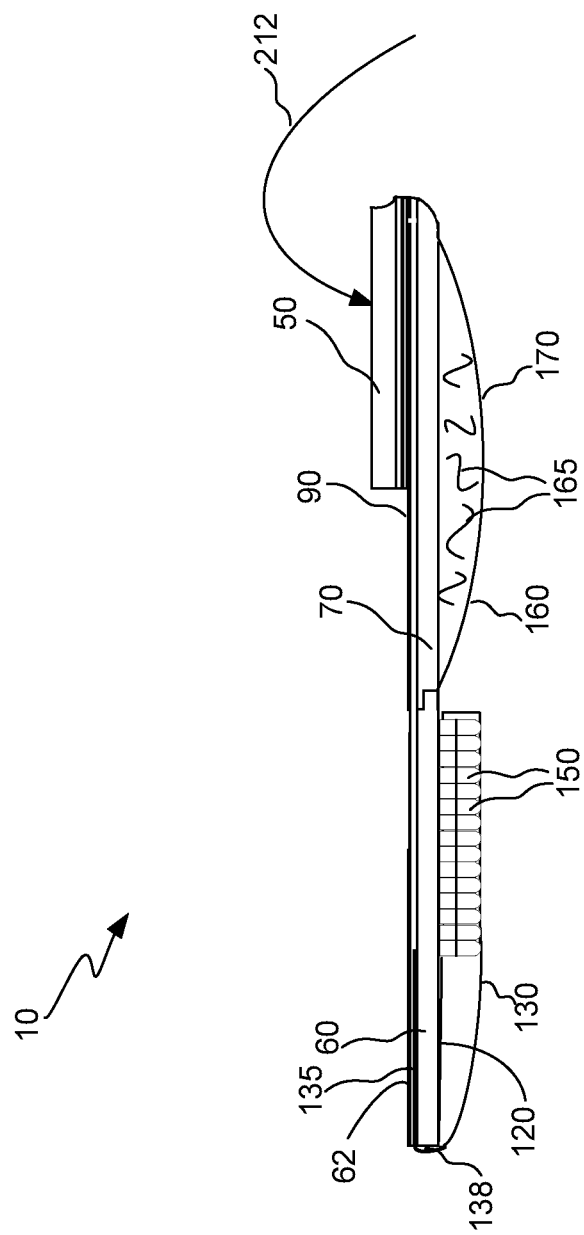
FIG. 14 is a view in elevation of the first embodiment portable female urine collector, this view showing the proximal end portion folded against the center portion of the portable female urine collector.
Figure 15:
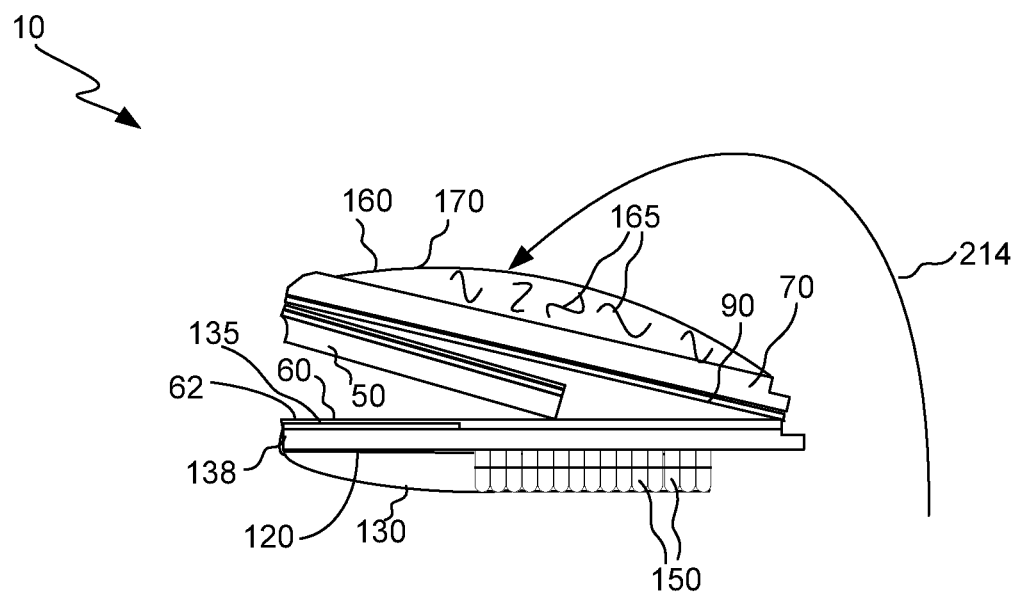
FIG. 15 is a view in elevation of the first embodiment portable female urine collector, this view showing the proximal end portion and the center portion of the portable female urine collector folded against the distal end portion of the portable female urine collector.
Figure 16:
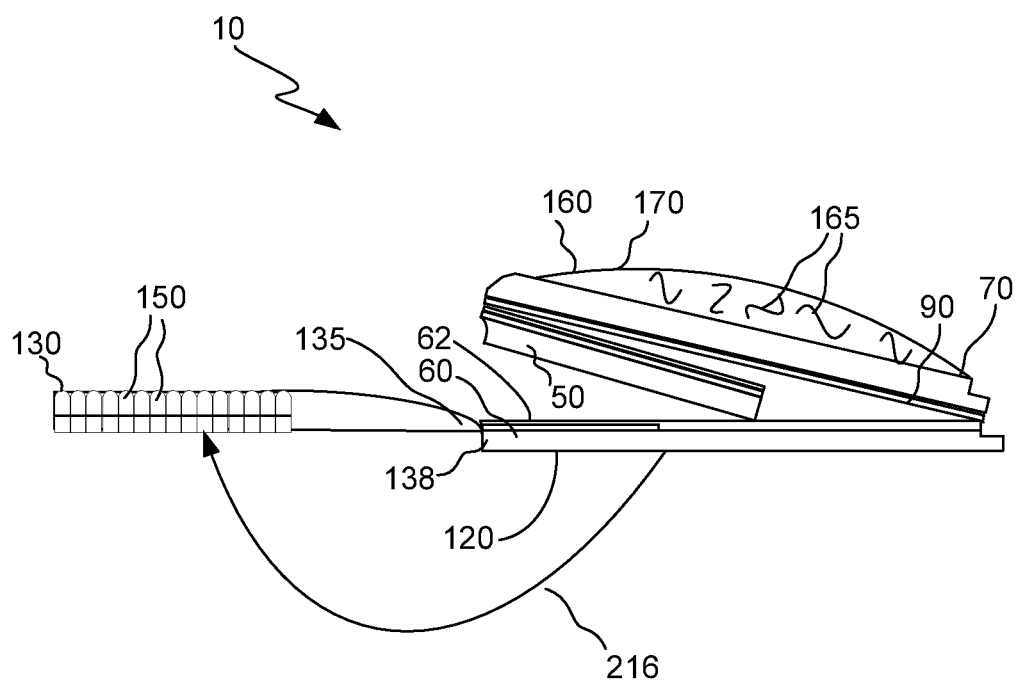
FIG. 16 is a view in elevation of the first embodiment portable female urine collector, this view showing the proximal end portion and the center portion of the portable female urine collector folded against the distal end portion of the portable female urine collector, this view also showing the receptacle rotated into position to be expanded.
Figure 17:
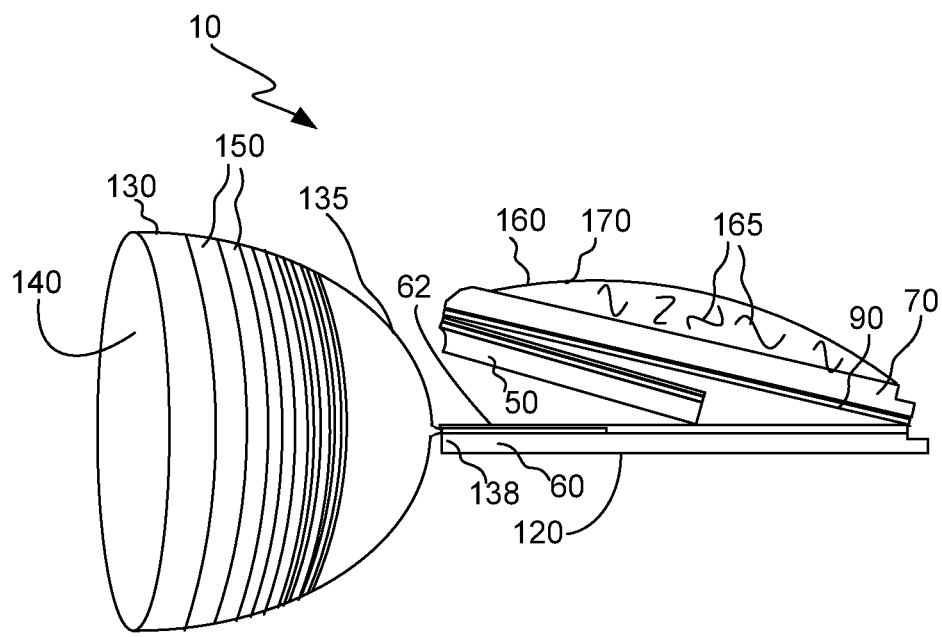
FIG. 17 is a view in elevation of the first embodiment portable female urine collector, this view showing the receptacle in an expanded state and prior to being pulled-back or inverted to receive the folded proximal end portion, the folded center portion and the distal end portion of the first embodiment portable female urine collector.
Figure 18:
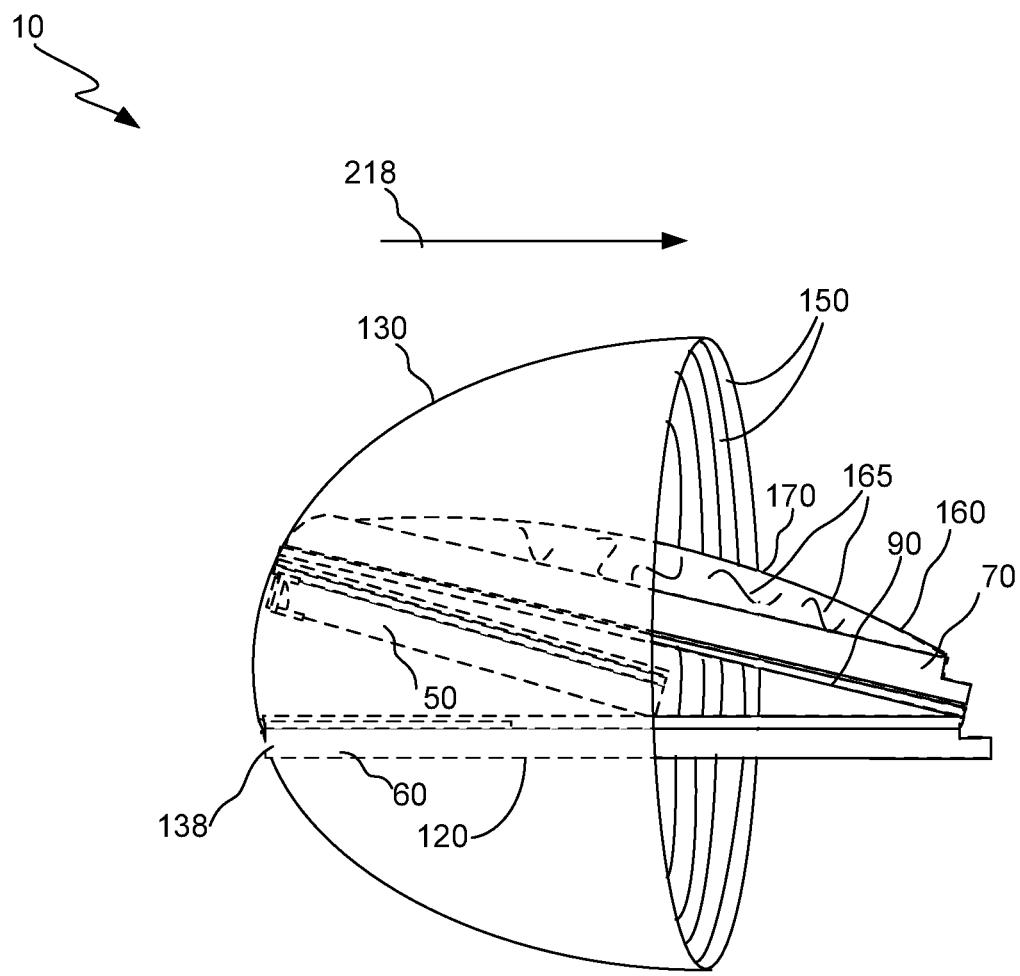
FIG. 18 is a view in elevation of the first embodiment portable female urine collector, this view showing the receptacle in an expanded state and being pulled-back or inverted to receive the folded proximal end portion, the folded center portion and the distal end portion of the first embodiment portable female urine collector.
Figure 19:
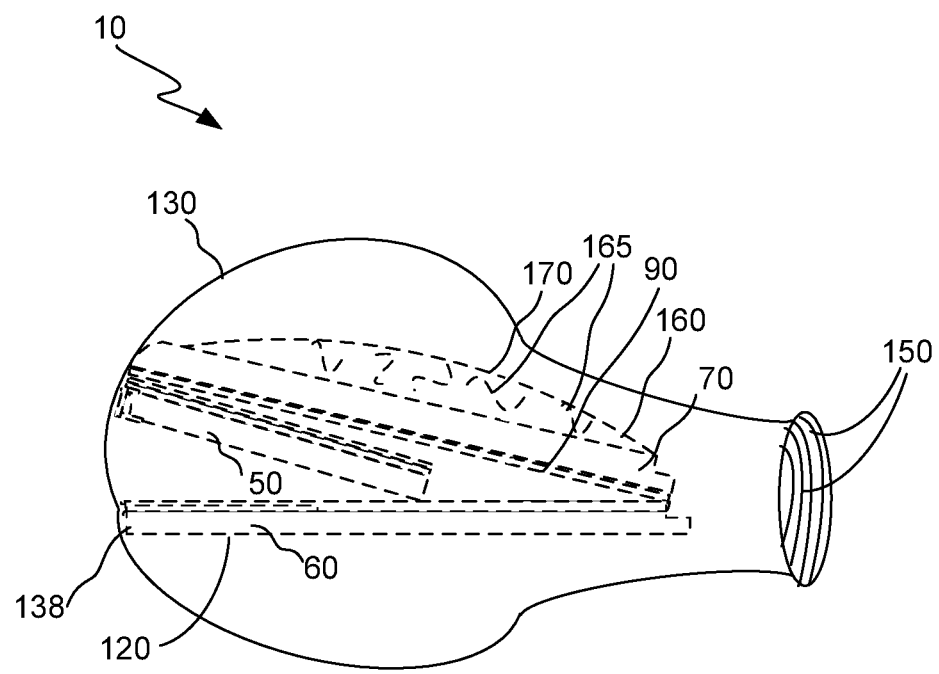
FIG. 19 is a view in elevation of the first embodiment portable female urine collector, this view showing the receptacle in an expanded state and after being pulled-back or inverted to receive the folded proximal end portion, the folded center portion and the distal end portion of the first embodiment portable female urine collector.
Figure 20:
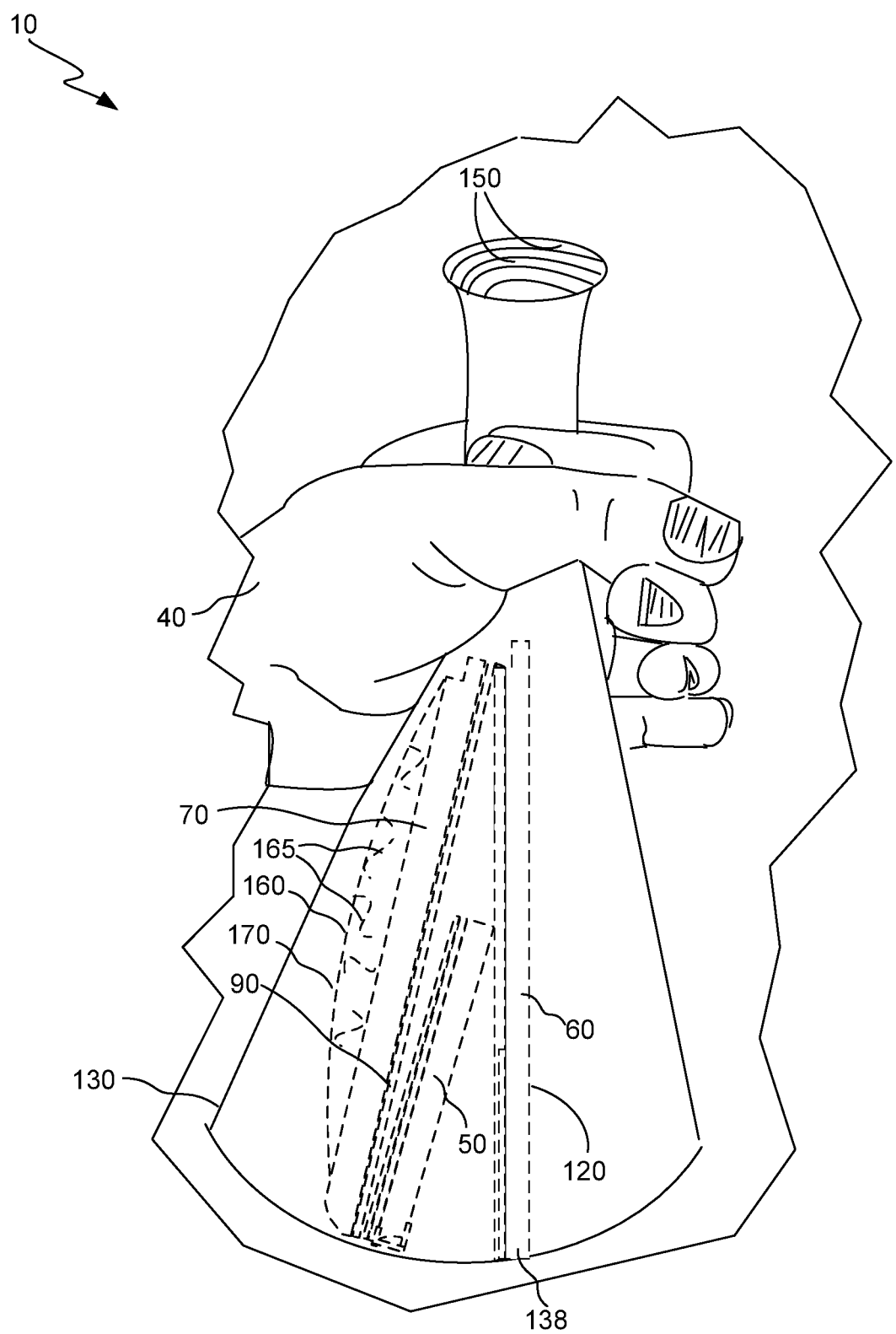
FIG. 20 is a view in perspective of the first embodiment portable female urine collector, this view showing the receptacle in an expanded state and after being pulled-back or inverted to receive the folded proximal end portion, the folded center portion and the distal end portion of the first embodiment portable female urine collector, this view also showing the open end portion of the receptacle being grasped by a hand of the user in preparation for stowing the folded proximal end portion, the folded center portion and the distal end portion within the receptacle.

Referring to FIGS. 11 and 12, there is shown a fourth embodiment portable female urine collector, generally referred to as 200, for urine collection and stowage. Fourth embodiment portable female urine collector 200 (herein referred to as "fourth embodiment urine collector 200") is substantially similar to first embodiment urine collector 10, except second layer 110 comprises a plurality of disks 210 stacked one upon the other for sequentially absorbing the urine and for sequentially expanding as the plurality of disks 210 sequentially absorb the urine. In this regard, plurality of disks 210 will expand in the direction of third layer 170 to intimately engage and expand third layer 170 as plurality of disks 210 absorb urine. Fourth embodiment urine collector 200 provides an alternative embodiment to first embodiment urine collector 10.

With reference to FIGS. 13, 14, 15, 16, 17, 18, 19, 20, and 21, after urine collection, proximal end portion 50 and center portion 70 belonging to any of first, second, third and fourth embodiment urine collectors 10/180/190/200, respectively, are foldable toward distal end portion 60 for stowage in receptacle 130. Stowage of proximal end portion 50, distal end portion 60 and center portion 70 in receptacle 130 will be described with reference to first embodiment urine collector 10, it being understood that the description applies to second, third and fourth embodiments urine collectors 180/190/200, as well. In this regard, proximal end portion 50 is pivoted or folded in the direction of a directional arrow 212 and center portion 70 is pivoted or folded in the direction of a directional arrow 214. After urine collection, hand 40 holding first embodiment urine collector 10 can grab and fold first embodiment urine collector 10, as described immediately hereinabove, while the available hand grasps and rotates receptacle 130 away from bottom surface 120 in the direction of a directional arrow 216. Receptacle 130 is opened by the available hand, after receptacle 130 is rotated or while receptacle 130 is being rotated into position. After receptacle 130 is opened, the available hand inverts receptacle 130 and pulls receptacle 130 over folded center portion 70, folded proximal end portion 50 and distal end portion 60 in the direction of a directional arrow. This results in folded proximal end portion 50, folded center portion 70 and distal end portion 60 being placed into receptacle 130. At this point, both hands are used to tie the open portion of receptacle 130 into a knot 219, so as to substantially seal folded proximal end portion 50, folded center portion 70 and distal end portion 60 in receptacle 130.

Figure 21:
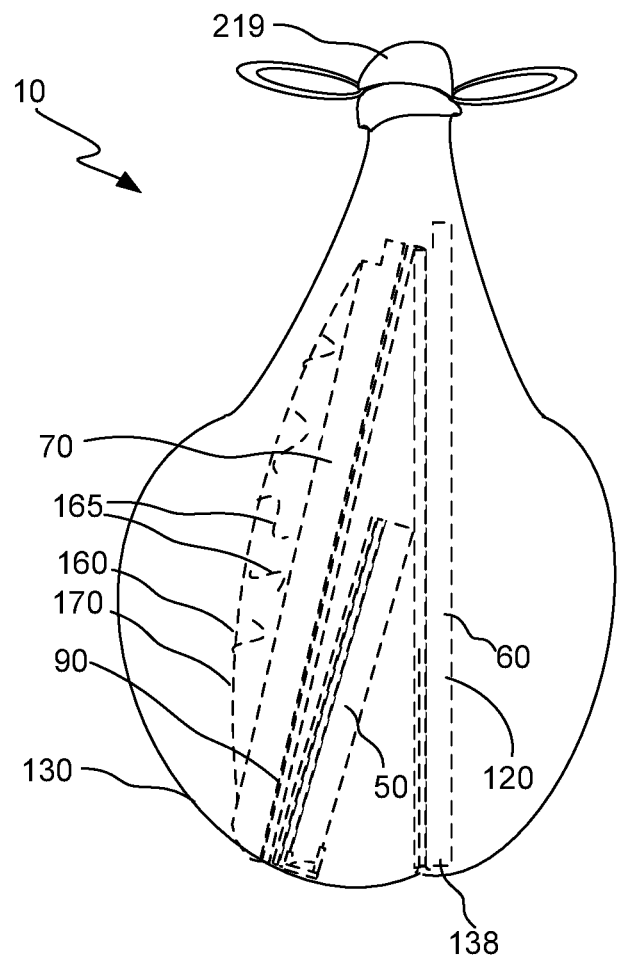
FIG. 21 is a view in perspective of the first embodiment portable female urine collector, wherein the proximal end portion, the center portion and the distal end portion of the portable female urine collector are stowed in the receptacle for disposal.

Thus, as shown in FIG. 21, center portion 70, proximal end portion 50 and distal end portion 60 belonging to any of first, second, third and fourth embodiment urine collectors 10/180/190/200, respectively, are stowed in receptacle 130 for convenient and hygienic disposal of the urine collector after use.

Illustrative Methods

An illustrative method associated with exemplary embodiments for assembling a portable female urine collector for urine collection and stowage will now be described.

Figure 22:
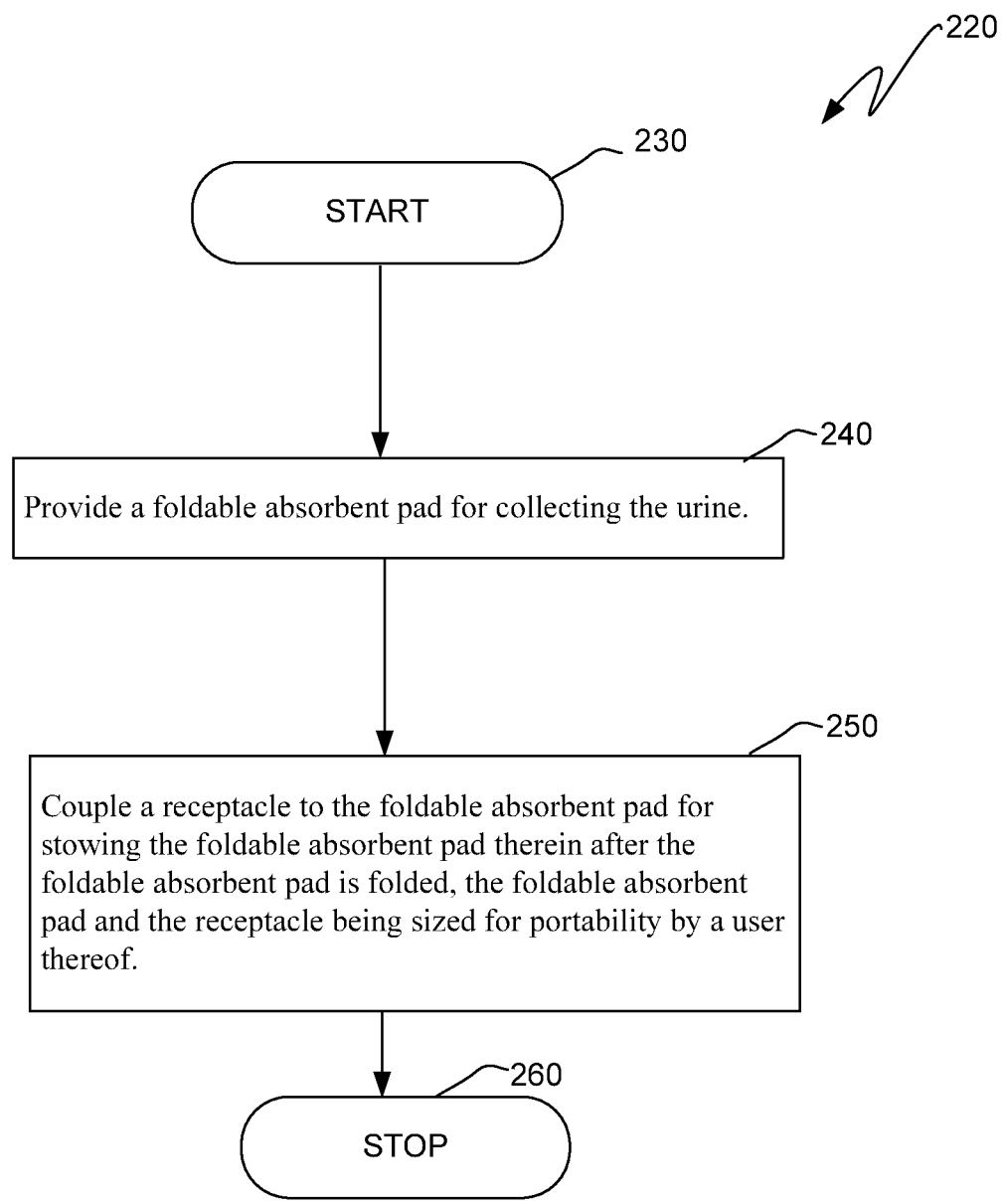
FIG. 22 is a flowchart of an illustrative method of assembling a portable female urine collector for urine collection and stowage.

Referring to FIG. 22, an illustrative method 220 that is provided for assembling a portable female urine collector for urine collection and stowage starts at a block 230. At a block 240, a foldable absorbent pad for collecting the urine is provided. At a block 250, a receptacle is coupled to the foldable absorbent pad for stowing the foldable absorbent pad therein after the foldable absorbent pad is folded, the foldable absorbent pad and the receptacle being sized for portability by a user thereof. The method stops at a block 260.

Other modifications and implementations will occur to those skilled in the art without departing from the spirit and the scope of the invention as claimed. For example, proximal end portion 50 of any of the previously mentioned embodiments may have a transverse accordion configuration that can be manually compressed and expanded, so as to allow proximal end portion 50 to be shortened and lengthened in an accordion-like fashion. Such a transverse accordion configuration would enhance the ability of the invention to assume a more compact shape before use, if desired. Accordingly, the description hereinabove is not intended to limit the invention, except as indicated in the following claims.

Therefore, provided herein are a portable female urine collector for urine collection and stowage and a method of assembling same.

What is claimed is:

1. A hand-held female urine collector, the hand-held female urine collector including:
    a proximal end portion;
    a distal end portion;
    a center portion for collecting urine, the center portion being located between, and coupled to, the proximal and distal end portions, the center portion including a plurality of layers, the plurality of layers including:
    a urine-permeable first layer for wicking the urine away from a urine discharge area of a user;
    a urine-absorbing second layer intimately contacting the urine-permeable first layer for absorbing the urine wicked away from the urine discharge area of the user, the urine-absorbing second layer being disk-shaped for radially and axially expanding as the urine-absorbing second layer absorbs the urine; and
    a urine-impermeable third layer disposed adjacent to the urine-absorbing second layer for restricting the urine to the urine-absorbing second layer wherein the proximal and distal end portions are configured to provide support for the urine collecting center portion when held by a user during urine collection.

2. The hand-held female urine collector of claim 1, further comprising a receptacle, coupled to an exterior surface of the distal end portion, the receptacle configured upon deployment, to stow the proximal end, center and distal end portions of said urine collector therein after urine collection is complete.

3. The hand-held female urine collector of claim 2, wherein
    the receptacle is configured to acquire an unexpanded state during urine collection for unobstructed collection of the urine; and
    the receptacle is configured to be deployed into an expanded state after urine collection for stowing the proximal end, distal end and center portions within the receptacle.

4. The hand-held female urine collector of claim 3, wherein the receptacle, prior to deployment, is configured as a pocket guide for receiving a user's fingers to facilitate placement and support of the urine collecting center portion at a urine discharge area of the user during urine collection.

5. The hand-held female urine collector of claim 1, wherein the urine-absorbing second layer includes an absorbent powder.

6. The hand-held female urine collector of claim 1, wherein the urine-absorbing second layer includes an absorbent gel.

7. The hand-held female urine collector of claim 1, wherein the proximal end portion defines a wiping surface thereon for wiping the urine away from a urine discharge area of the user after urine collection.

8. A hand-held female urine collector, the hand-held female urine collector including:
    a proximal end portion;
    a distal end portion;
    a center portion for collecting urine, the center portion being located between, and coupled to, the proximal and distal end portions, the center portion including a plurality of layers, the plurality of layers including:
    a urine-permeable first layer for wicking the urine away from a urine discharge area of a user;
    a urine-absorbing second layer intimately contacting the urine-permeable first layer for absorbing the urine wicked away from the urine discharge area of the user;
    a urine-impermeable third layer disposed adjacent to the urine-absorbing second layer for restricting the urine to the urine-absorbing second layer wherein the proximal and distal end portions are configured to provide support for the urine collecting center portion when held by a user during urine collection,
    wherein the urine-absorbing second layer includes a plurality of disks stacked one upon the other for sequentially absorbing the urine and for sequentially expanding as the plurality of disks sequentially absorb the urine; and
    wherein the urine-impermeable third layer is contoured to expand as the plurality of disks sequentially expand.

9. A hand-held female urine collector including:
    a proximal end portion;
    a distal end portion;
    a center portion for collecting urine, the center portion being located between, and coupled to, the proximal and distal end portions, the center portion including:
    a urine-permeable first layer for wicking the urine away from a urine discharge area of a user;
    an expandable urine-absorbing second layer intimately contacting the urine permeable first layer for absorbing the urine wicked away from the urine discharge area of the user, the urine-absorbing second layer being disk-shaped for radially and axially expanding as the urine-absorbing second layer absorbs the urine;
    a urine-impermeable third layer disposed immediately adjacent to the urine absorbing second layer for restricting the urine to the urine-absorbing second layer, the urine-impermeable third layer being adapted to expand as the urine-absorbing second layer absorbs the urine and expands; and
    a receptacle connected to the proximal end portion for stowing the proximal end, distal end and center portions therein after urine collection is complete,
    wherein the proximal and distal end portions are configured to provide support for the urine collecting center portion when held by a user during urine collection.

10. The hand-held female urine collector of claim 9, wherein said urine collector is configured to:
    assume an unfolded state, wherein the proximal end, distal end and center portions are in axial alignment with one another, before collecting the urine; and
    assume a folded state after collecting the urine to facilitate stowing.

11. The hand-held female urine collector of claim 9, wherein the urine-absorbing second layer includes an absorbent powder.

12. The hand-held female urine collector of claim 9, wherein the urine-absorbing second layer includes an absorbent gel.

13. The hand-held female urine collector of claim 9, wherein the urine-absorbing second layer includes a plurality of disks stacked one upon the other for sequentially absorbing the urine and for sequentially expanding as the plurality of disks sequentially absorb the urine.

14. A method of assembling a hand-held female urine collector for urine collection and stowage, wherein the hand-held female urine collector comprises:
- a proximal end portion;
- a distal end portion;
- a center portion for collecting urine, the center portion being located between, and coupled to, the proximal and distal end portions, the center portion including a plurality of layers, the plurality of layers including:
- a urine-permeable first layer for wicking the urine away from a urine discharge area of a user;
- a urine-absorbing second layer intimately contacting the urine-permeable first layer for absorbing the urine wicked away from the urine discharge area of the user, the urine-absorbing second layer being disk-shaped for radially and axially expanding as the urine-absorbing second layer absorbs the urine; and
- a urine-impermeable third layer disposed adjacent to the urine-absorbing second layer for restricting the urine to the urine-absorbing second layer wherein the proximal and distal end portions are configured to provide support for the urine collecting center portion when held by a user during urine collection;

the method including:

coupling a receptacle to the plurality of layers.

* * * * *